(12) United States Patent
Pais et al.

(10) Patent No.: US 11,660,599 B2
(45) Date of Patent: May 30, 2023

(54) SAMPLE EXTRACTION DEVICE AND METHODS OF USE THEREOF (71) Applicant: NOVEL MICRODEVICES, LLC, Annapolis, MD (US)

(72) Inventors: Andrea Maria Dominic Pais, Annapolis, MD (US); Rohan Joseph Alexander Pais, Annapolis, MD (US); Chelsea Qinjie Zhou, Annapolis, MD (US)

(73) Assignee: NOVEL MICRODEVICES, INC., Baltimore, MD (US)

( * ) Notice: Subject to any disclaimer, the term of this patent is extended or adjusted under 35 U.S.C. 154(b) by 1336 days.

(21) Appl. No.: 15/747,436

(22) PCT Filed: Jul. 25, 2016

(86) PCT No.: PCT/US2016/043855
§ 371 (c)(1),
(2) Date: Jan. 24, 2018

(87) PCT Pub. No.: WO2017/019598
PCT Pub. Date: Feb. 2, 2017

(65) Prior Publication Data
US 2018/0372595 A1 Dec. 27, 2018

Related U.S. Application Data (60) Provisional application No. 62/331,635, filed on May 4, 2016, provisional application No. 62/261,577, filed
(Continued)

(51) Int. Cl.
*B01L 3/02* (2006.01)
*B01L 3/00* (2006.01)
(Continued)

(52) U.S. Cl.
CPC ........ *B01L 3/50273* (2013.01); *B01F 31/441* (2022.01); *B01F 33/30* (2022.01);
(Continued)

(58) Field of Classification Search
CPC ..... B01L 2400/0481; B01L 2400/0683; B01L 2200/0689; B01L 2200/16; B01L 3/50273;
(Continued)

(56) References Cited

U.S. PATENT DOCUMENTS 4,789,639 A 12/1988 Fleming
8,747,004 B1 6/2014 McPherson et al.
(Continued)

FOREIGN PATENT DOCUMENTS

CN 1448715 A 10/2003
CN 1639555 A 7/2005
(Continued)

*Primary Examiner* — Young J Kim
(74) *Attorney, Agent, or Firm* — FisherBroyles, LLP (57) ABSTRACT The presently disclosed subject matter provides devices and methods for sample extraction from a swab during biological sample processing. In particular embodiments, the devices and methods are configured for use in conjunction with microfluidic devices for sample processing.

24 Claims, 10 Drawing Sheets

Related U.S. Application Data on Dec. 1, 2015, provisional application No. 62/196,816, filed on Jul. 24, 2015.

(51) Int. Cl.

| | | |
|---|---|---|
| *G01N 33/487* | (2006.01) | |
| *B01L 7/00* | (2006.01) | |
| *G01N 1/38* | (2006.01) | |
| *B01F 31/441* | (2022.01) | |
| *B01F 33/30* | (2022.01) | |
| *B01F 33/452* | (2022.01) | |
| *B01F 33/301* | (2022.01) | |
| *G01N 1/10* | (2006.01) | |
| *G01N 35/00* | (2006.01) | |

(52) U.S. Cl.
CPC ........ *B01F 33/3017* (2022.01); *B01F 33/452* (2022.01); *B01L 3/0293* (2013.01); *B01L 3/502738* (2013.01); *B01L 7/00* (2013.01); *B01L 7/52* (2013.01); *G01N 1/10* (2013.01); *G01N 1/38* (2013.01); *G01N 33/487* (2013.01); *B01L 3/50825* (2013.01); *B01L 3/502715* (2013.01); *B01L 2200/027* (2013.01); *B01L 2200/0689* (2013.01); *B01L 2200/16* (2013.01); *B01L 2300/045* (2013.01); *B01L 2300/0681* (2013.01); *B01L 2300/0816* (2013.01); *B01L 2300/0867* (2013.01); *B01L 2300/1827* (2013.01); *B01L 2400/0478* (2013.01); *B01L 2400/0481* (2013.01); *B01L 2400/0605* (2013.01); *B01L 2400/0683* (2013.01); *G01N 2035/00128* (2013.01); *G01N 2035/00237* (2013.01); *G01N 2035/00534* (2013.01)

(58) Field of Classification Search
CPC .... B01L 3/502738; G01N 2035/00128; G01N 1/38; G01N 2035/00534; G01N 33/487
See application file for complete search history.

(56) References Cited

U.S. PATENT DOCUMENTS

| | | | |
|---|---|---|---|
| 2003/0109057 A1 | 6/2003 | DiCesare et al. | |
| 2005/0272113 A1* | 12/2005 | Mosher | C12Q 1/37 435/23 |
| 2008/0190391 A1 | 8/2008 | McElwee et al. | |
| 2008/0206740 A1* | 8/2008 | Skiffington | G01N 1/02 435/5 |
| 2009/0075344 A1 | 3/2009 | Green | |
| 2010/0056383 A1 | 3/2010 | Ririe et al. | |
| 2010/0317093 A1 | 12/2010 | Turewicz et al. | |
| 2012/0167672 A1 | 7/2012 | Miller | |
| 2012/0168305 A1 | 7/2012 | Hunter | |
| 2013/0309136 A1 | 11/2013 | Johnson et al. | |
| 2014/0194305 A1 | 7/2014 | Kayyem et al. | |
| 2014/0243706 A1 | 8/2014 | El-Fahmawi | |
| 2015/0076008 A1 | 3/2015 | Athanasiou et al. | |

FOREIGN PATENT DOCUMENTS

| | | | | |
|---|---|---|---|---|
| CN | 1882835 A | 12/2006 | | |
| CN | 1921803 A | 2/2007 | | |
| CN | 201376965 Y | 1/2010 | | |
| CN | 103394410 | 11/2013 | | |
| CN | 103562727 | 2/2014 | | |
| CN | 104203411 A | 12/2014 | | |
| DE | 102009035941 | 2/2011 | | |
| DE | 102010036216 A1 | 3/2012 | | |
| EP | 1024354 A1 | 8/2000 | | |
| EP | 2007651 A2 | 12/2008 | | |
| JP | H06313767 | 11/1994 | | |
| JP | 2002105100 | 4/2002 | | |
| JP | 2009128037 A | 6/2006 | | |
| JP | 2013217707 A | 10/2013 | | |
| JP | 2013228235 A | 11/2013 | | |
| JP | 2014533176 | 12/2014 | | |
| JP | 2015513102 A | 4/2015 | | |
| WO | WO-2005071388 A1 * | 8/2005 | ............ | B01L 3/5029 |
| WO | 2007129463 A2 | 11/2007 | | |
| WO | 2008076395 A2 | 6/2008 | | |
| WO | 2009006641 | 1/2009 | | |
| WO | 2014049371 A2 | 4/2014 | | |
| WO | 2014149277 A2 | 9/2014 | | |
| WO | 2015075447 A1 | 5/2015 | | |
| WO | 2016027782 A1 | 2/2016 | | |

\* cited by examiner

SAMPLE EXTRACTION DEVICE AND METHODS OF USE THEREOF

CROSS-REFERENCE TO RELATED APPLICATIONS

The present application is a 371 national phase entry of international application PCT/US2016/043855, filed Jul. 25, 2016, which claims priority to provisional patent application No. 62/331,635, filed May 4, 2016; U.S. Provisional Application No. 62/261,577 filed Dec. 1, 2015; and U.S. Provisional Application No. 62/196,816, filed Jul. 24, 2015; the entire contents of which are incorporated by reference herein in their entireties.

BACKGROUND

Swabs are largely used as biological sample collection devices. While swabs such as the COPAN FLOQSwabs™ are engineered such that the entire sample stays close to the surface for fast and complete elution, physical forces need to be used to maximize the elution of the sample into the transfer medium or buffer. Typically, manual agitation by vigorously shaking the swab in the transport medium or vortexing is used in laboratories to maximize the elution of the sample from the swab into solution. The swab is manually expressed and the solution containing the sample is then pipetted out and processed further depending on the type of assay.

In Point-of-Care ("POC") and low resource settings, vortexing samples is not a convenient method for eluting samples in liquid medium and manual shaking can result in operator to operator inconsistencies. Moreover, since swabs are absorbent, a finite amount of sample in solution is lost as it remains on the swab. In cases where the analyte is present in very low concentrations, this can result in reduced sensitivity due to insufficient amounts of analyte being eluted from the swab into the solution.

In microfluidic systems where reagent volumes are minimized, concentrating more of the analyte in a smaller volume enables the addition of more analyte into the system in the same volume. However, for such microfluidic systems it is necessary to squeeze out the liquid from swabs in order to maximize the amount of sample extracted from the swab.

Accordingly, there is a need for improved devices and methods for sample extraction.

SUMMARY

In accordance with the present invention, various embodiments of sample extraction devices and methods of use thereof are disclosed. In one embodiment, a sample extraction device is provided comprising:

a swab shaft comprising a first end, a stopper, and a second end;

a lid attached to the first end of the swab shaft, wherein the lid is slidable along the swab shaft;

a crush O-ring on the inside of the lid;

a swab tip at the second end of the swab shaft; and a sample extraction container comprising a liquid medium and a squeezing structure, wherein the squeezing structure comprises an opening smaller than the swab tip.

In some embodiments of the sample extraction device of the present invention, the lid is a screw top lid or a press fit lid. In other embodiments, the squeezing structure is an O-ring. In other embodiments, the liquid medium is located between two frangible seals.

In other embodiments, the sample extraction container further comprises an outlet port. In other embodiments, the outlet port is fluidically connected to a microfluidic device through a fitting connector. In other embodiments, the fitting connector is a luer, screw, press fitting, or snap fitting. In other embodiments, the microfluidic device comprises a sharp structure capable of breaking a frangible seal in the sample extraction container to allow transfer of the liquid medium into the microfluidic device. In other embodiments, the sample extraction device further comprises a check valve between the sample extraction container and the microfluidic device to prevent backflow of the liquid medium. In other embodiments, the microfluidic device further comprises a filter, a semipermeable membrane, or a porous membrane to filter out undesirable materials. In other embodiments, the microfluidic device further comprises a microfluidic cartridge with on-board stored reagents in reagent pouches, an integrated nucleic acid lateral flow strip for detection, and one or more actuator elements.

In other embodiments, the sample extraction device further comprises a ring-shaped heater that forms a jacketed sheath around the sample extraction container. In other embodiments, the heater is a resistive heating element comprising a resistor embedded in a block of thermally conducting material. In other embodiments, the heater is a resistive thin-film heater or a peltier element. In other embodiments the heater is a positive temperature coefficient self-regulating element. In other embodiments, the heater comprises a phase change material in a sealed pouch.

In other embodiments, the squeezing structure comprises a narrow sleeve, wherein the narrow sleeve is configured to form a tight fit around the swab head and thereby deform and squeeze the swab head when it is inserted into the squeexing structure. In other embodiments, the liquid medium is fluidically connected to the top of the sleeve via a channel. In other embodiments, the squeezing structure comprises an O-ring and the sample extraction container comprises a piston plunger. In other embodiments, the sample extraction container further comprises a spring-loaded pestle and a grate.

In other embodiments, a method for sample extraction from a swab tip is provided comprising the use of any of the sample extraction device described herein comprising the steps of:

a. inserting the swab tip into the sample extraction container;

b. pushing the swab tip through the squeezing structure and into the liquid medium;

c. sliding the lid along the swab shaft and closing the lid, thereby forming an airtight seal between the swab shaft and the sample extraction container;

d. pulling the swab tip out until the stopper makes contact with the inside of the lid; and e. connecting the sample extraction device to an inlet on a microfluidic device. In some embodiments, steps (c) and (d) are repeated one or more times.

In other embodiments, the swab shaft of any of the sample extraction devices described herein is a breakable swab shaft comprising a scored breakpoint. In further embodiments, a method for sample extraction from a swab tip is provided comprising the use of sample extraction devices described herein comprising a breakable swab shaft, wherein the method comprises the steps of:

a. opening the lid of the sample extraction container;

b. inserting the swab tip through the squeezing structure and into the liquid medium;

c. pulling the swab tip back out of through the squeezing structure;

d. breaking the breakable swab shaft at the scored breakpoint and allowing the swab tip to rest atop the squeezing structure;

e. closing the lid of the sample extraction container; and f. connecting the sample extraction device to an inlet on a microfluidic device.

In some embodiments, steps (b) and (c) are repeated one or more times.

Certain aspects of the presently disclosed subject matter having been stated hereinabove, which are addressed in whole or in part by the presently disclosed subject matter, other aspects will become evident as the description proceeds when taken in connection with the accompanying Examples and Figures as best described herein below.

BRIEF DESCRIPTION OF THE FIGURES

Having thus described the presently disclosed subject matter in general terms, reference will now be made to the accompanying Figures, which are not necessarily drawn to scale.

DETAILED DESCRIPTION

The presently disclosed subject matter now will be described more fully hereinafter with reference to the accompanying Figures, in which some, but not all embodiments of the presently disclosed subject matter are shown. Like numbers refer to like elements throughout. The presently disclosed subject matter may be embodied in many different forms and should not be construed as limited to the embodiments set forth herein; rather, these embodiments are provided so that this disclosure will satisfy applicable legal requirements. Indeed, many modifications and other embodiments of the presently disclosed subject matter set forth herein will come to mind to one skilled in the art to which the presently disclosed subject matter pertains having the benefit of the teachings presented in the foregoing descriptions and the associated Figures. Therefore, it is to be understood that the presently disclosed subject matter is not to be limited to the specific embodiments disclosed and that modifications and other embodiments are intended to be included within the scope of the appended claims.

Sample Extraction Device and Methods

The disclosed invention is for extracting the material collected on a swab sample. Swab samples are a commonly used method to collect biological material needed for diagnostic testing. These samples could be collected at a prior time than when the testing is performed or at the time of the testing. The biological material trapped on the swab may vary in viscosity, dryness, solid content and adhesion to the swab.

Described herein are methods and devices for maximizing sample elution from a swab during biological sample processing. In one embodiment, the sample preparation method first involves inserting the swab into a sample extraction container (SEC) containing a buffer relevant to the sample processing step. The container dimensions are selected such that the tip of the swab can be completely immersed in the volume of buffer required for performing the assay. This hydrates the swab and serves to loosen the biological material trapped on it. To facilitate the extraction of the sample from the swab, the container comprises one or more structures at instances below and at the liquid level of the buffer. The dimensions and shape of the structures are selected such that they form a tight fit and restrain the squeeze the swab tip as it is pushed down into the SEC and pulled up from it. The dimensions and shape of the structures at the liquid level are so designed such they form a tight fit with the swab tip as it moves through it, thus squeezing the liquid and solid material out of the swab.

Figure 1:
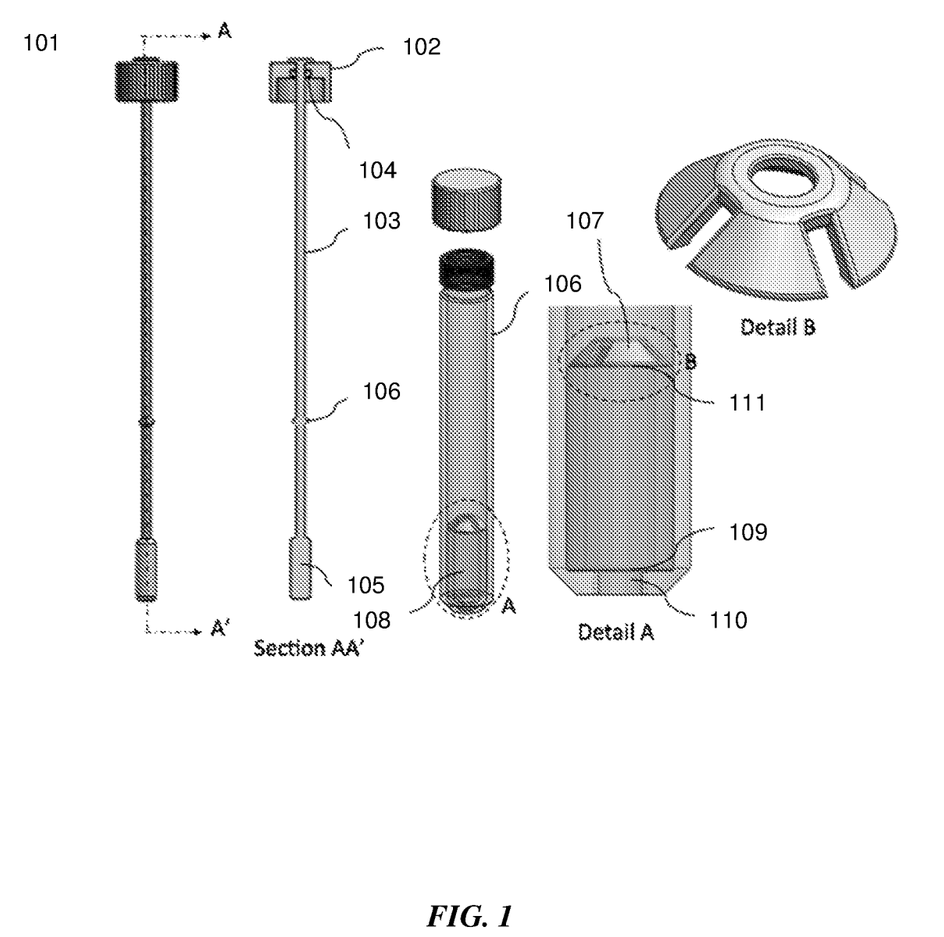
FIG. 1 shows sectional and detailed views of an exemplary sample extraction device for swab sample extraction.

Referring to FIG. 1, sectional and detailed views of a sample extraction unit 101 are shown for swab sample extraction. In one embodiment, a screw top or press fit lid 102 is attached on the swab shaft 103 as depicted in section AA'. A crush O-ring 104 is present on the inside of the lid and the interface between the swab shaft and lid. The swab can be inserted into the sample extraction container 106 that contains a liquid medium or buffer to elute the sample into. The lid on the swab shaft is able to slide up and down on the shaft. When the lid is tightened, the O-ring is crushed to make an airtight seal with the sample extraction container and the swab shaft. The sample that needs to be extracted is present on the swab tip 105. As depicted in Detail A, the sample extraction container has a squeezing structure 107 with an opening smaller than the swab tip, such that the swab tip is deformed and squeezed and as it is pushed through it. This forces the collected sample to detach from the swab and elute into the solution contained in the bottom unit 108 of the sample extraction container. A non-limiting example of the shape of the squeezing structure is shown in Detail B. In some embodiments, the squeezing structure may be an O-ring. The squeezing structure may be designed based on the shape, structure and material of the swab. To extract the sample on the from the swab tip, the user places the swab into the swab extraction container, closes the sliding lid and pulls the swab shaft back out until the stopper 106 makes contact with the bottom of the lid. The bottom of the sample extraction container is sealed with a frangible or pierceable seal material 109 and may have a fitting with an outlet port 110 that allows it to be connected to a fluidic unit such as a microfluidic cartridge, for further processing. In some embodiments a top frangible seal 111 may be present, such that the liquid medium inside the sample extraction container is stored within the volume between the two frangible seals. This works to prevent movement and sticking of the liquid to the lid and walls during shipping, transport and before use, and constrain the liquid medium to the bottom of the sample extraction container. The frangible seal may be ruptured by the swab, to release its liquid contents when the swab is inserted into the sample extraction container.

Figure 2:
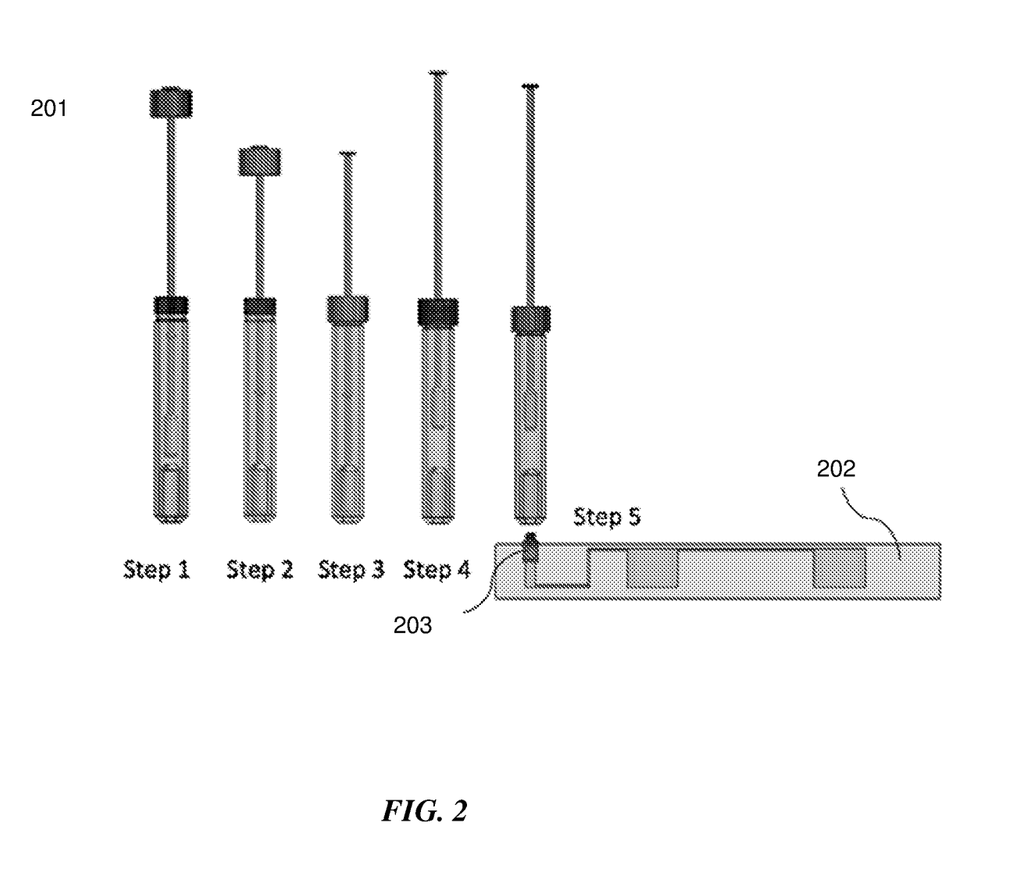
FIG. 2 shows an exemplary step by step sequence for sample extraction from a swab sample.

Referring to FIG. 2, a step by step sequence 201 for sample extraction from a swab sample is shown. Step 1—the swab is inserted into the sample extraction container; Step 2—the swab is pushed down through the squeezing structure into the solution contained at the bottom of the sample extraction container. This also causes the solution to be displaced from the bottom and rise so as to completely immerse and hydrate the swab tip. Step 3—the lid attached to the swab shaft is slid down and closed so as to form an airtight seal between the swab shaft and the sample extraction container. Step 4—the swab is pulled out until the stopper makes contact with the bottom of the lid. This causes the swab to be squeezed out so as to prevent it from absorbing the solution containing the sample, that it was immersed and hydrated in. Steps 3 and 4 can be repeated multiple times if required to maximize the sample elution efficiency and can also function to homogenize the sample. Step 5—the sample extraction device is then connected to an inlet on the microfluidic device 202 through a fitting 203 on the microfluidic device.

Figure 3:
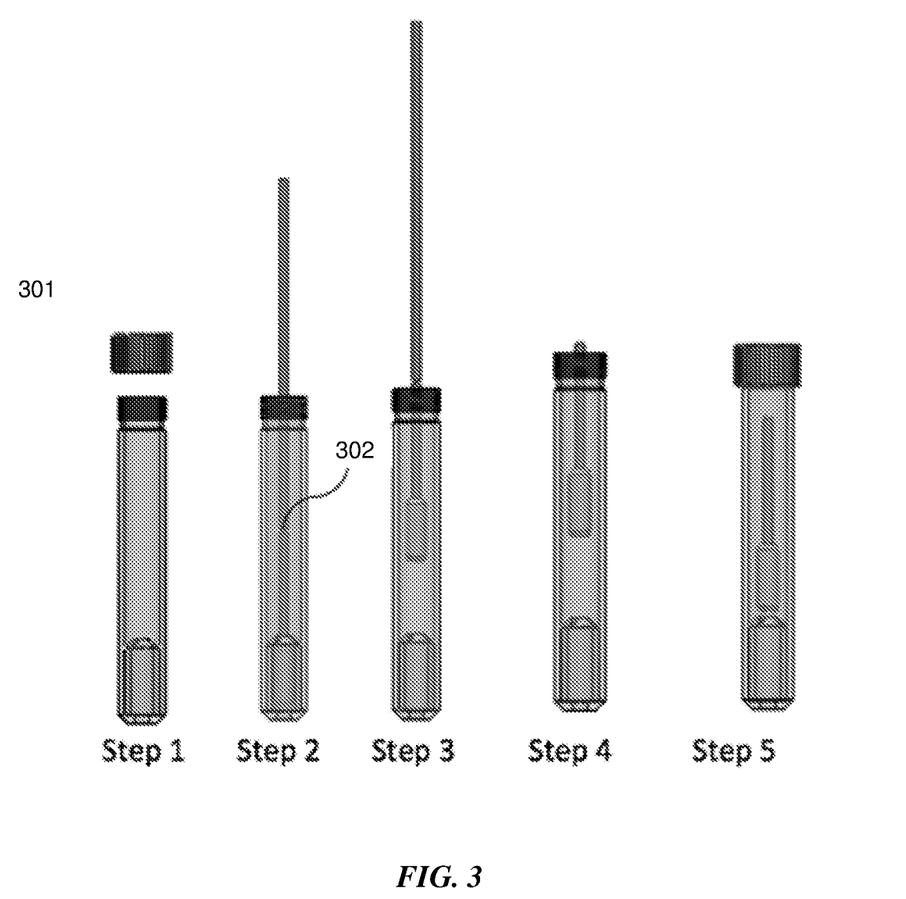
FIG. 3 shows an exemplary step by step sequence for sample extraction from a swab with a breakable shaft.

In an alternative embodiment, a swab with a breakable shaft may be used. A step by step sequence 301 for sample extraction from a swab with a breakable shaft is depicted in FIG. 3. Step 1—the lid of the sample extraction container is opened. Step 2—the swab is inserted completely into the sample extraction container through the squeezing structure. Step 3—the swab is pulled up through the squeezing structure. Step 2 and 3 may be repeated multiple times if necessary to homogenize the sample. After the swab is squeezed out, the shaft is broken at the scored breakpoint 302 in Step 4 and the lid of the sample extraction container is closed in Step 5. The swab sits above the squeezing structure and does not come in contact with the solution below it. The sample extraction container is then connected to the microfluidic device to enable the transfer of its contents into it.

Figure 4:
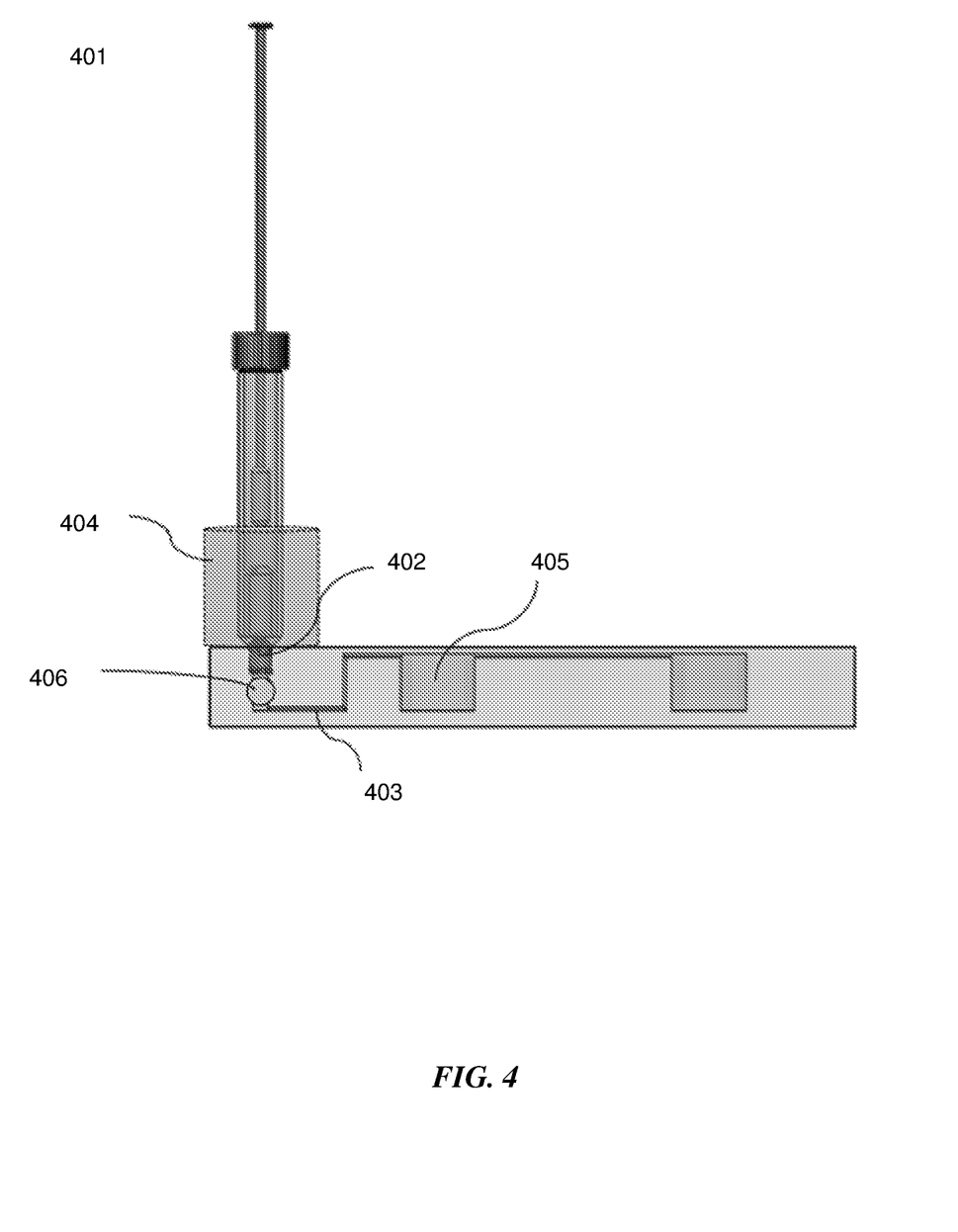
FIG. 4 shows a side view of an exemplary sample extraction container connected to a microfluidic device with an integrated heater.

As seen in FIG. 4, the outlet port of the swab extraction chamber makes fluidic connection to the microfluidic device 401 through a fitting connector 402 such as a luer, screw, press or snap fitting. The microfluidic device may contain a sharp structure such as a needle or pin that can break or pierce the frangible material on the bottom of the sample extraction container so as to enable its contents to be transferred into the microfluidic device. Alternatively the twisting or pressing forces applied when connecting the sample extraction container to the fitting on the microfluidic device can rupture the frangible material sealing it. A check valve 406 may be present on the microfluidic device at the interface between the sample extraction container and the fluidic conduit 403 connecting to a fluidic well 405, so as to prevent backflow of the contents. In some embodiments, a filter, semipermeable or porous membrane may be present on the microfluidic device to filter out undesirable materials in the sample extraction container that may inhibit the downstream diagnostic assay from entering into the microfluidic device. The filter or membrane may be placed anywhere on the microfluidic device in the path between the inlet from the sample extraction container into the microfluidic device and the outlet of the fluidic conduit into a fluidic well 405.

Figure 8:
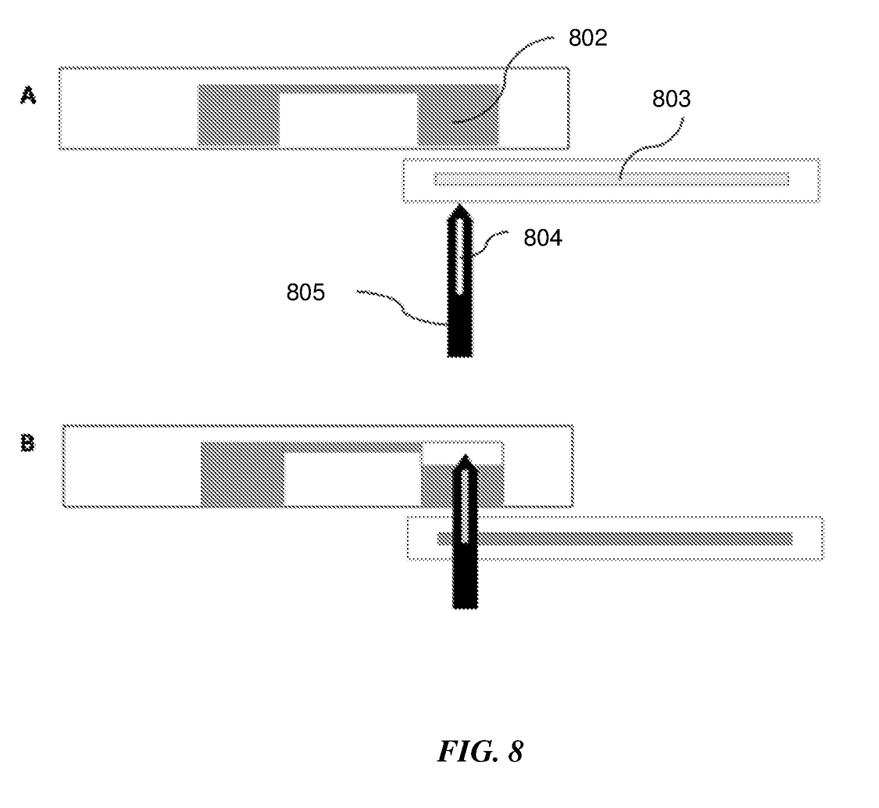
FIG. 8 shows the principle of fluidic transfer on a microfluidic device, from a fluidic well to a lateral flow strip using an actuated lancet.

Moving fluids in a microfluidic device is a challenging task, requiring the use of sophisticated pumps, and actuators. In an exemplary embodiment, heat energy may be used to pressurize the sample extraction container, causing the sample to be transferred into the microfluidic device. Heating at the same time may also be used to lyse cells to release nucleic acids for downstream Nucleic Acid Amplification Tests (NAATs), as well as for deactivating inhibitors present in the sample. In some embodiments a valve may be present on the microfluidic device that can be actuated to transfer the sample from the sample extraction container into the microfluidic device. This additional valve is advantageous when the sample needs to be heated for a predefined period of time before it can be transferred into the microfluidic device. The pressure built up in the sample extraction container then works to push the sample into the microfluidic device when the valve is actuated. As seen in FIG. 8, an exemplary ring-shaped heater 404 is present at the interface of the microfluidic device and the sample extraction container. The heater forms a jacketed sheath around the sample extraction container and is hollow at the bottom, thus allowing the sample extraction container to be connected to the microfluidic device. In one embodiment, the heater may be a resistive heating element comprising a resistor embedding in a block of thermally conducting material such as a metal, metal oxide or metal alloy. The heater may also be a resistive thin-film heater or a peltier element. In other embodiments the heater is a positive temperature coefficient self-regulating element. The heater may be integrated as part of the microfluidic device and intended as a single use, disposable element. In an additional embodiment, a phase change material may be used to generate the heat energy for lysis and sample transfer. Phase change materials are widely used for a variety of applications requiring thermal energy storage and have been developed for use across a broad range of temperatures (−40° C. to more than 150° C.). Phase change materials are advantageous because they offer high-density energy storage and store heat within a narrow temperature range. Additionally they are inexpensive, non-toxic and do not require electrical energy for generating heat. As such, they are an appealing choice for point-of-care settings and for single-use devices that require heat energy. In an additional embodiment a phase change material contained in a sealed pouch is used to form a jacketed sheath around the sample extraction container. The jacket of phase change material may either be present as part of the microfluidic device or as part of the sample extraction container. The act of connecting the sample extraction container to the microfluidic device works to create a nucleation site that in turn activates the phase change material, causing it to rise in temperature and heat the sample. This may be accomplished by packaging a metal piece in the pouch containing the phase change material, which snaps when the sample extraction container is connected to the microfluidic device. The phase change material may also be activated by an external actuator present on the actuating element in the microfluidic device. In some embodiments, a suitable phase change material may be activated to cool the sample so as to prevent its degradation. In some embodiments, the heater may serve to heat lyse and transfer the sample to the fluidic well on the microfluidic devices, as well as to run a NAAT on the microfluidic device.

In an additional embodiment, a chemical reaction that releases a gas or an exothermic reaction, occurring in the lid of the sample extraction container may be used to pressurize the container and transfer the sample into a second fluidic chamber.

Figure 5:
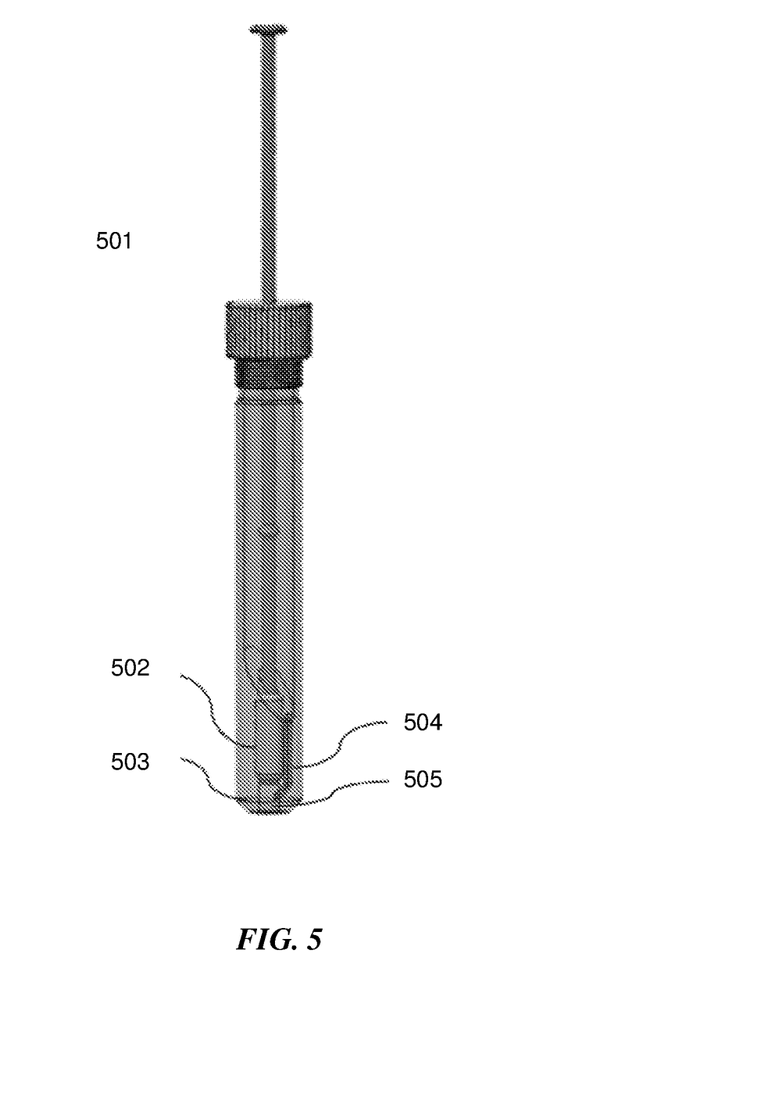
FIG. 5 shows a schematic of a sample extraction container with a tight fitting sleeve to squeeze and deform a swab.

In an additional embodiment shown in FIG. 5, the squeezing structure may be a narrow sleeve 502 that forms a tight fit around the swab head thus, deforming and squeezing the swab head when it is inserted into it. As the swab is pushed into the tight fitting sleeve, the sample is squeezed out from the surface of the swab and collects on the top of the sleeve. The liquid medium inside the sample extraction container flows to the top of the sleeve through the channel 504. Repeated pushing and pulling through the tight fitting sleeve can be done to homogenize the sample and maximize elution. The sample extraction container has a frangible or pierceable membrane seal 503 at the bottom and an outlet 505 that can connect to a second fluidic device.

Figure 6A:
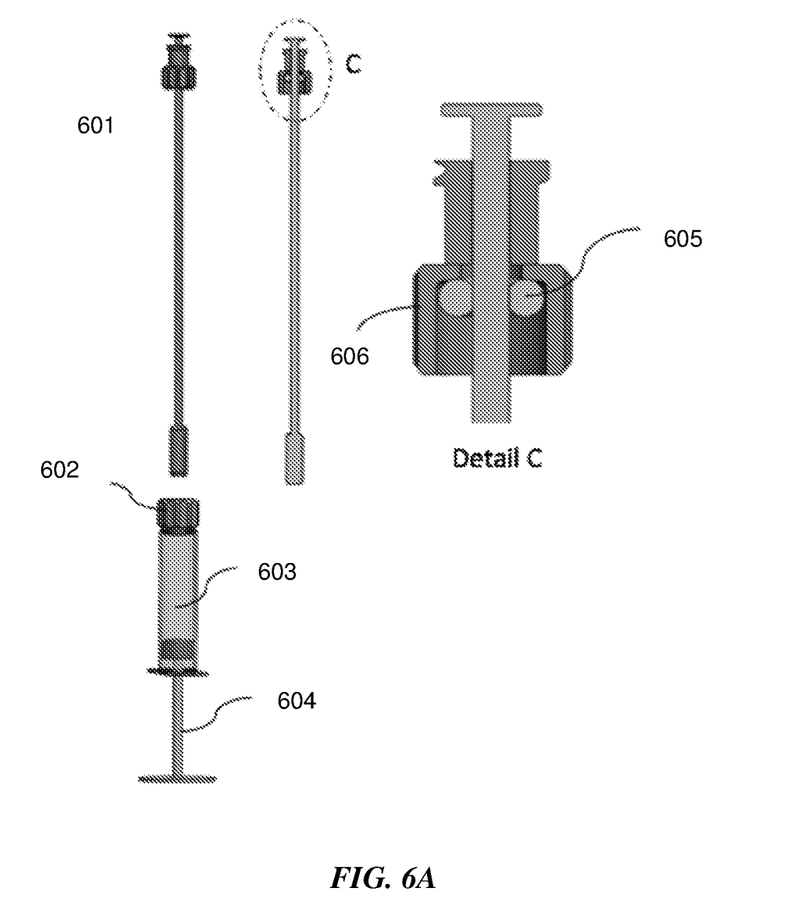
FIG. 6A shows a schematic of a sample extraction device with a piston plunger for swab sample extraction.
Figure 6B:
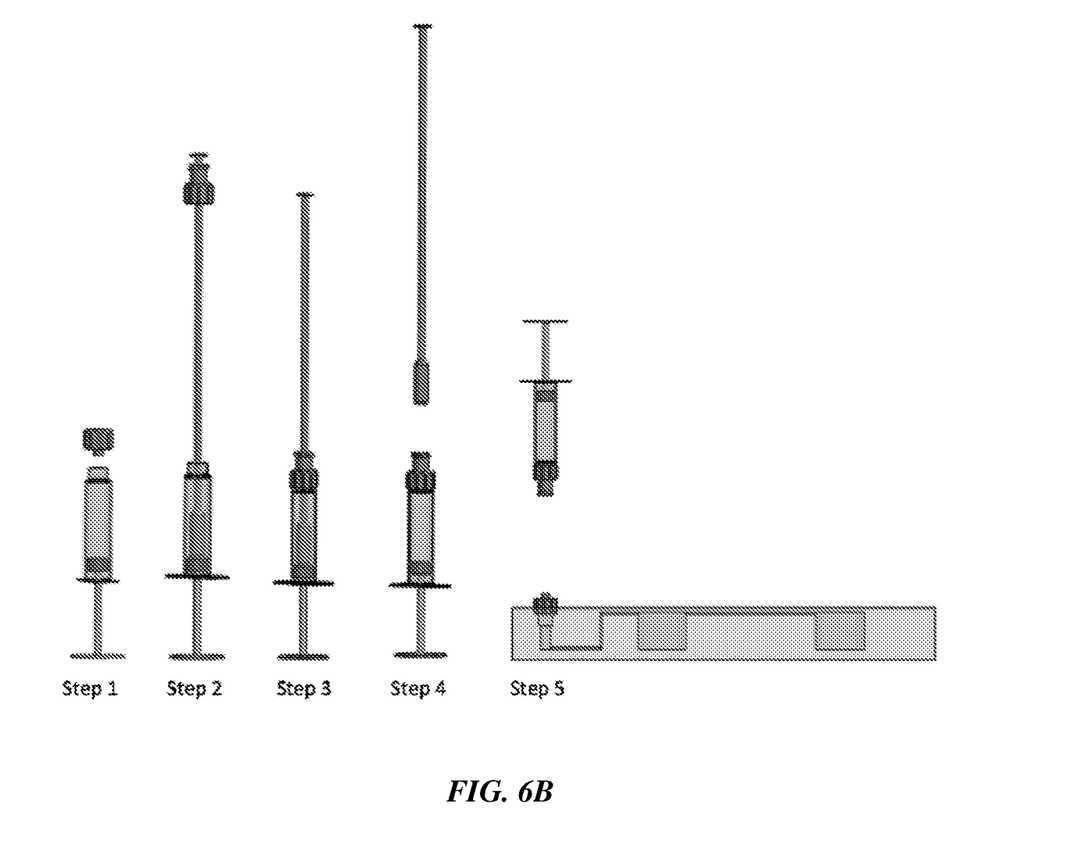
FIG. 6B shows the step by step sequence for swab sample extraction on an exemplary sample extraction device with a piston plunger

In an additional embodiment of a sample extraction device 601 for swab sample extraction shown in FIG. 6A, the squeezing structure for squeezing out the sample and liquid from the swab is an O-ring 605 that is part of the connector 606 attached to the swab shaft, as seen in Detail C. The sample extraction container has a piston plunger 604 on one end and is filled with the liquid medium or buffer 603 for eluting the sample on the swab and capped with a lid 602. FIG. 6B shows the step by step sequence for swab sample extraction, on an exemplary sample extraction device with a piston plunger that is mechanically/manually actuated. In some embodiments the piston plunger may be pneumatically actuated, such as by using a squeezable bulb to push air and displace the plunger.

While NAATs are highly sensitive and specific, their implementation has been restricted largely to laboratories. This is so because NAATs are complex tests that require skilled labor and expensive laboratory equipment to perform. Recent advances in isothermal amplification assay technologies have simplified the instrumentation requirements for performing NAATs. However, true sample-to-answer systems still require automation of assay steps that rely on external instrumentation. Sample preparation is seen the bottleneck for performing NAATs and methods to simplify and automate the steps for sample preparation for NAATs are required to facilitate their implementation in point of care settings. The modules of the invention disclosed here can be integrated to perform sample-to-answer automation of a NAAT for point of care settings.

Figure 7:
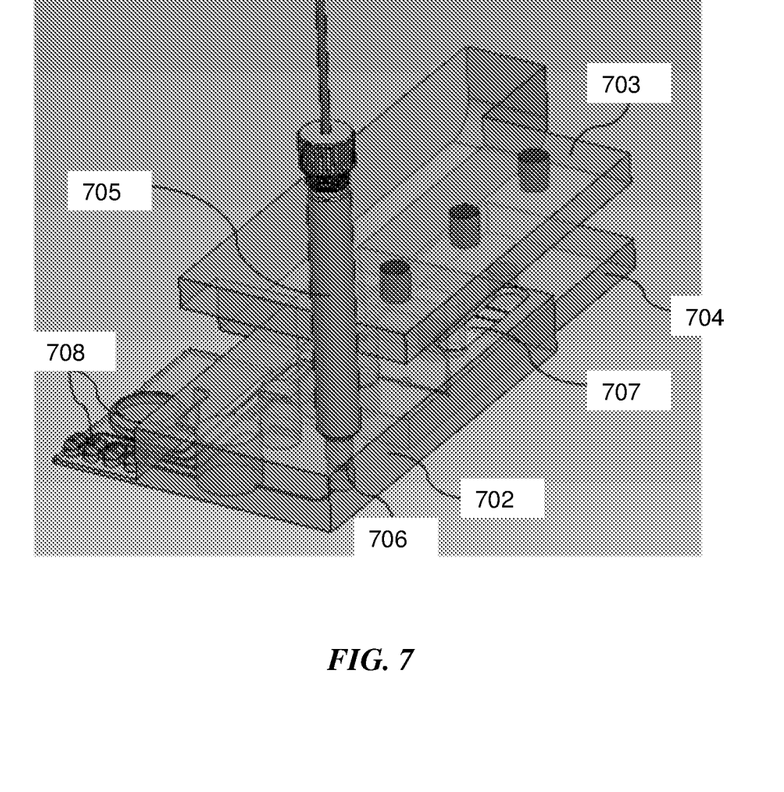
FIG. 7 shows a schematic representation of an integrated microfluidic device for a sample-to-answer Nucleic Acid Amplification Test (NAAT) assay from a swab sample.

In an exemplary embodiment a sample-to-answer nucleic acid amplification assay may be performed on a swab sample. FIG. 7 is a schematic representation of an integrated microfluidic device for a sample-to-answer NAAT assay from a swab sample.

The microfluidic device comprises a microfluidic cartridge 702 with on-board stored reagents in reagent pouches 708, an integrated nucleic acid lateral flow strip 707 for detection, top actuator element 703 and bottom actuator element 704. The swab sample is inserted into the sample extraction container 705 on the microfluidic device and the swab is squeezed dry by one of the methods described in the various embodiments in this disclosure, thereby eluting the sample into a cell lysis buffer stored inside the sample extraction container. Heating the sample extraction container causes cell lysis, as well as the pressure built up in the container forces the lysate through a fluidic conduit into a fluidic well on the microfluidic device, containing magnetic beads for nucleic acid extraction and purification. A filter 706 is present on the microfluidic device to filter out inhibitors and only allow nucleic acids to enter the well containing binding buffer and magnetic beads. As the microfluidic cartridge slides in proximity to the actuator elements, a predefined assay sequence is automatically performed. The sequence may be designed by the user depending on the assay requirements. An exemplary sequence is as follows: binding buffer, wash buffer 1, wash buffer 2, elution buffer are dispensed from the stored reagent pouches and filled in parallel into their respective fluidic wells. Following the dispensing of the miscible reagents, an immiscible liquid such as mineral oil is dispensed such that the miscible reagents form a fluidic circuit without mixing with each other since they are separated from each other by an immiscible oil phase.

Magnetic beads with ionizable groups that have a net positive charge at a given pH are used for binding DNA. An example of such as type of magnetic bead is the ChargeSwitch Magnetic bead (Life Technologies, Inc. Carlsbad, Calif.). DNA binds to such a type of magnetic bead in the presence of a binding buffer capable of creating a net positive charge on the bead and DNA is eluted in the presence of an elution buffer capable of creating a net neutral or negative charge on the bead. In this embodiment, ChargeSwitch magnetic beads that cause DNA to bind to them in the presence of a buffer having a pH<5 and elute from them in the presence of a buffer having a pH>8 are used. The magnetic beads are sequentially moved through all the wells on the microfluidic cartridge by methods described in this disclosure. DNA is first allowed to bind to the magnetic beads in the presence of a binding buffer. The beads are then moved in and out of two wells containing wash buffer to wash the impurities from the beads. The impurities are left behind in the wash buffer solution. The washed beads are then moved to a well containing elution buffer where the DNA is eluted from the beads into the elution buffer. The eluted DNA may then be used to hydrate lyophilized reagents for a Nucleic Acid Amplification Test (NAAT). In some embodiments, the magnetic beads may be eluted directly into the amplification well. One or more heaters is turned on as part of the automation sequence to supply the temperatures for amplification.

Various methods of detection can be used for detecting the amplified products, including visual detection using pH sensitive dyes or metal-sensitive indicators, electrochemical detection, optical detection using intercalating dyes or fluorescent probes, turbidimetry, lateral flow strip detection. In this example a lateral flow strip is used to detect the amplified nucleic acids. Biotin and FAM/FITC modified FIP and BIP primers respectively may be used in the LAMP reaction. A sandwich format lateral flow test may be used. The amplified product may be mixed with a dilution or running buffer before lateral flow strip detection. A valve may be present and actuated as part of the assay automation sequence to allow the amplified products to flow on the lateral flow strip. Alternatively, a septum may be pierced to allow the amplified product to flow on the lateral flow strip.

In one embodiment a lancet with a hollow channel or a needle may be actuated by the actuating element to pierce the wall of the amplification chamber and transfer the fluid to a lateral flow strip for detection. FIG. 8 describes the principle of moving liquid product containing the analyte to be detected, from the fluidic well 802 to a lateral flow strip 803. FIG. 8A shows the lancet 805 with a hollow channel 804 before actuation. FIG. 8B shows the hollow lancet after actuation, where it pierces through the lateral flow strip and the bottom of the fluidic well thus creating a conduit for fluid flow to the lateral flow strip.

Figure 9:
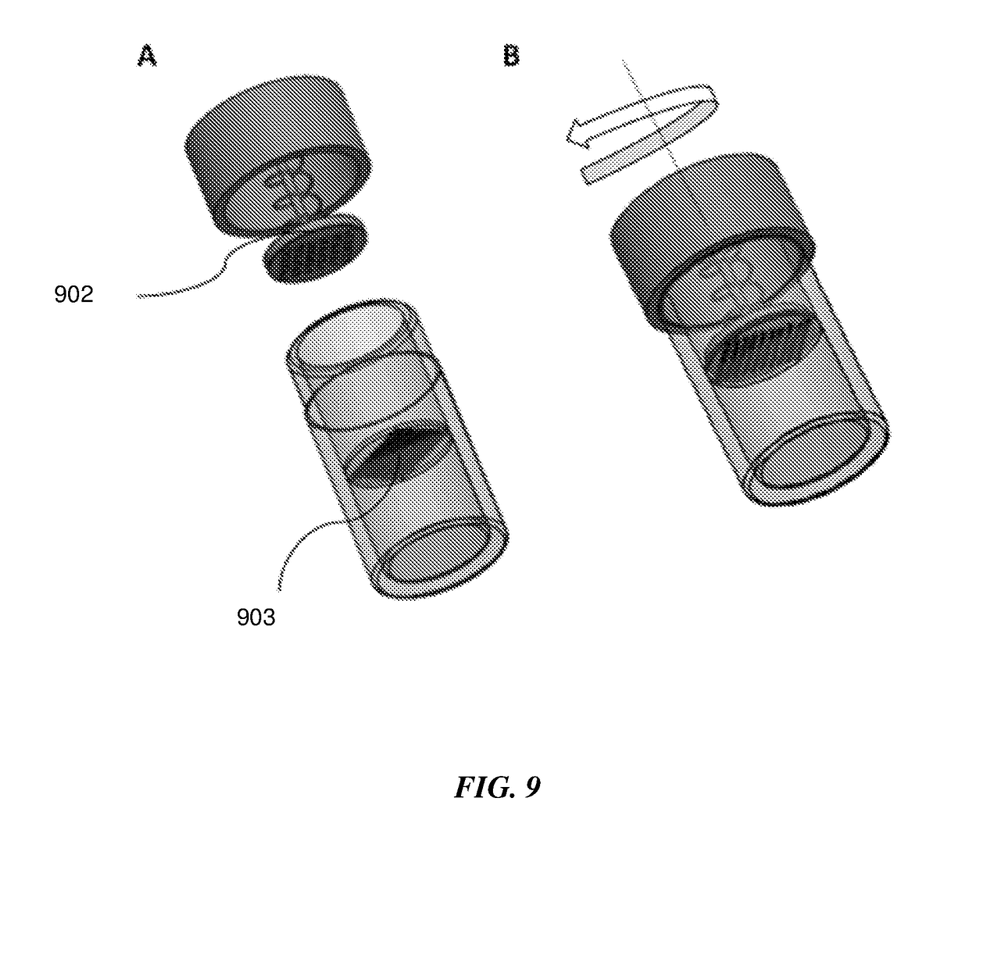
FIG. 9 shows a schematic of an embodiment of a sample extraction container with spring-loaded pestle and grate, for sample homogenization.

For some samples such as tissue, plant, food, soil and small organisms, swabs may not be the sample collection devices of choice. Additionally, these samples need to be homogenized during sample preparation. FIG. 9 shows an embodiment of a sample extraction container with a spring-loaded pestle 902 attached to the lid. A grate 903 comprising numerous tiny holes, serrations, blades and the like, selected based on the sample is present inside the container. The container may be filled with a buffer such as lysis buffer or liquefaction buffer. The act of turning the lid to close the container compresses the spring, thereby pushing the pestle onto the bottom grate while the lid is being screwed shut. Any sample material trapped between the pestle and the grate gets compressed, crushed and sheared, due to the relative motion between the pestle and the grate as the lid is being twisted shut. The prepared homogenized sample in buffer may then be transferred for further downstream processing either in a fluidic cartridge or other system.

Depending on the application and user requirements, the sample processing system may integrate motors, actuators, heating elements, thermocouples, fans, cooling units, microcontrollers, optical detectors, electrodes, filters, light sources, battery packs, wireless modules, and electronics such that it forms a single, self-contained, self-sufficient integrated system for performing biological sample processing. The volume of reagent pouches, reservoirs and fluidic wells may vary depending on the bioassay and the needs of the user. Typical volumes can range from 1 ul to 10 ml or from 5 ul to 1 ml.

There are many suitable materials for the microfluidic device. Plastics such as thermoplastic materials are a good choice for a single use disposable device due to their low cost and ability to be mass produced.

Suitable materials for the fully integrated sample-to-answer microfluidic device include materials such as glass, polypropylene, polycarbonate, PMMA, COC, silicon or a combination of one or more of the materials. A microfluidic device may be polymer injection molded with integrated silicon or glass MEMS functionalized electrode array or a microarray, or a lateral flow strip for detection. The material may be chosen based on the requirements of the user and the assay being performed on it, based on its biocompatibility, chemical compatibility.

The footprint of the microfluidic device may range from a few square millimeters to few tens of square centimeters depending on the user requirements and the sample processing application. In some embodiments, multiple microfluidic devices may be stacked or arrayed and processed in parallel. The pull forces, shapes and sizes of the permanent magnets in the sample processing system may be chosen depending on the sample processing needs, shape, size, volume, material properties and rupture pressure of frangible seal. The frangible seal materials include aluminum foils, polymers, rubber, metals, adhesive tapes, metal oxides or a combination of materials.

General Definitions

Although specific terms are employed herein, they are used in a generic and descriptive sense only and not for purposes of limitation. Unless otherwise defined, all technical and scientific terms used herein have the same meaning as commonly understood by one of ordinary skill in the art to which this presently described subject matter belongs.

"Nucleic acid" as used herein means a polymeric compound comprising covalently linked subunits called nucleotides. A "nucleotide" is a molecule, or individual unit in a larger nucleic acid molecule, comprising a nucleoside (i.e., a compound comprising a purine or pyrimidine base linked to a sugar, usually ribose or deoxyribose) linked to a phosphate group.

"Polynucleotide" or "oligonucleotide" or "nucleic acid molecule" are used interchangeably herein to mean the phosphate ester polymeric form of ribonucleosides (adenosine, guanosine, uridine or cytidine; "RNA molecules" or simply "RNA") or deoxyribonucleosides (deoxyadenosine, deoxyguanosine, deoxythymidine, or deoxycytidine; "DNA molecules" or simply "DNA"), or any phosphoester analogs thereof, such as phosphorothioates and thioesters, in either single-stranded or double-stranded form. Polynucleotides comprising RNA, DNA, or RNA/DNA hybrid sequences of any length are possible. Polynucleotides for use in the present invention may be naturally-occurring, synthetic, recombinant, generated ex vivo, or a combination thereof, and may also be purified utilizing any purification methods known in the art. Accordingly, the term "DNA" includes but is not limited to genomic DNA, plasmid DNA, synthetic DNA, semisynthetic DNA, complementary DNA ("cDNA"; DNA synthesized from a messenger RNA template), and recombinant DNA (DNA that has been artificially designed and therefore has undergone a molecular biological manipulation from its natural nucleotide sequence).

"Amplify," "amplification," "nucleic acid amplification," or the like, refers to the production of multiple copies of a nucleic acid template (e.g., a template DNA molecule), or the production of multiple nucleic acid sequence copies that are complementary to the nucleic acid template (e.g., a template DNA molecule).

The terms "top," "bottom," "over," "under," and "on" are used throughout the description with reference to the relative positions of components of the described devices, such as relative positions of top and bottom substrates within a device. It will be appreciated that the devices are functional regardless of their orientation in space.

Following long-standing patent law convention, the terms "a," "an," and "the" refer to "one or more" when used in this application, including the claims. Thus, for example, reference to "a subject" includes a plurality of subjects, unless the context clearly is to the contrary (e.g., a plurality of subjects), and so forth.

Throughout this specification and the claims, the terms "comprise," "comprises," and "comprising" are used in a non-exclusive sense, except where the context requires otherwise. Likewise, the term "include" and its grammatical variants are intended to be non-limiting, such that recitation of items in a list is not to the exclusion of other like items that can be substituted or added to the listed items.

For the purposes of this specification and appended claims, unless otherwise indicated, all numbers expressing amounts, sizes, dimensions, proportions, shapes, formulations, parameters, percentages, parameters, quantities, characteristics, and other numerical values used in the specification and claims, are to be understood as being modified in all instances by the term "about" even though the term "about" may not expressly appear with the value, amount or range. Accordingly, unless indicated to the contrary, the numerical parameters set forth in the following specification and attached claims are not and need not be exact, but may be approximate and/or larger or smaller as desired, reflecting tolerances, conversion factors, rounding off, measurement error and the like, and other factors known to those of skill in the art depending on the desired properties sought to be obtained by the presently disclosed subject matter. For example, the term "about," when referring to a value can be meant to encompass variations of, in some embodiments, ±100% in some embodiments ±50%, in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed methods or employ the disclosed compositions.

Further, the term "about" when used in connection with one or more numbers or numerical ranges, should be understood to refer to all such numbers, including all numbers in a range and modifies that range by extending the boundaries above and below the numerical values set forth. The recitation of numerical ranges by endpoints includes all numbers, e.g., whole integers, including fractions thereof, subsumed within that range (for example, the recitation of 1 to 5 includes 1, 2, 3, 4, and 5, as well as fractions thereof, e.g., 1.5, 2.25, 3.75, 4.1, and the like) and any range within that range.

All publications, patent applications, patents, and other references mentioned in the specification are indicative of the level of those skilled in the art to which the presently disclosed subject matter pertains. All publications, patent applications, patents, and other references are herein incorporated by reference to the same extent as if each individual publication, patent application, patent, and other reference was specifically and individually indicated to be incorporated by reference. It will be understood that, although a number of patent applications, patents, and other references are referred to herein, such reference does not constitute an admission that any of these documents forms part of the common general knowledge in the art.

Although the foregoing subject matter has been described in some detail by way of illustration and example for purposes of clarity of understanding, it will be understood by those skilled in the art that certain changes and modifications can be practiced within the scope of the appended claims.

That which is claimed:

1. A sample extraction device comprising:
   a swab shaft comprising a first end, a stopper, and a second end;
   a lid attached to the first end of the swab shaft, wherein the lid is slidable along the swab shaft;
   a crush O-ring on the inside of the lid;
   a swab tip at the second end of the swab shaft; and
   a sample extraction container comprising a liquid medium and a squeezing structure, wherein the squeezing structure comprises an opening smaller than the swab tip.

2. The sample extraction device of claim 1, wherein the lid is a screw top lid or a press fit lid.

3. The sample extraction device of claim 1, wherein the squeezing structure is an O-ring.

4. The sample extraction device of claim 1, wherein the liquid medium is located between two frangible seals.

5. The sample extraction device of claim 1, wherein the sample extraction container further comprises an outlet port.

6. The sample extraction device of claim 5, wherein the outlet port is fluidically connected to a microfluidic device through a fitting connector.

7. The sample extraction device of claim 6, wherein the fitting connector is a luer, screw, press fitting, or snap fitting.

8. The sample extraction device of claim 7, wherein the microfluidic device comprises a sharp structure capable of breaking a frangible seal in the sample extraction container to allow transfer of the liquid medium into the microfluidic device.

9. The sample extraction device of claim 7, further comprising a check valve between the sample extraction container and the microfluidic device to prevent backflow of the liquid medium.

10. The sample extraction device of claim 7, wherein the microfluidic device further comprises a filter, a semipermeable membrane, or a porous membrane to filter out undesirable materials.

11. The sample extraction device of claim 7, wherein the microfluidic device further comprises a microfluidic cartridge with on-board stored reagents in reagent pouches, an integrated nucleic acid lateral flow strip for detection, and one or more actuator elements.

12. The sample extraction device of claim 7, further comprising a ring-shaped heater that forms a jacketed sheath around the sample extraction container.

13. The sample extraction device of claim 12, wherein the heater is a resistive heating element comprising a resistor embedded in a block of thermally conducting material.

14. The sample extraction device of claim 12, wherein the heater is a resistive thin-film heater or a peltier element or a positive temperature coefficient (PTC) self regulating heater.

15. The sample extraction device of claim 12, wherein the heater comprises a phase change material in a sealed pouch.

16. The sample extraction device of claim 1, wherein the squeezing structure comprises a narrow sleeve, wherein the narrow sleeve is configured to form a tight fit around the swab head and thereby deform and squeeze the swab head when it is inserted into the squeezing structure.

17. The sample extraction device of claim 16, wherein the liquid medium is fluidically connected to the top of the sleeve via a channel.

18. The sample extraction device of claim 1, wherein the squeezing structure comprises an O-ring and the sample extraction container comprises a piston plunger.

19. The sample extraction device of claim 1, wherein the sample extraction container further comprises a spring-loaded pestle and a grate.

20. A method for sample extraction from a swab tip comprising the use of the sample extraction device of claim 1 comprising the steps of:
   a. inserting the swab tip into the sample extraction container;
   b. pushing the swab tip through the squeezing structure and into the liquid medium;
   c. sliding the lid along the swab shaft and closing the lid, thereby forming an airtight seal between the swab shaft and the sample extraction container;
   d. pulling the swab tip out until the stopper makes contact with the inside of the lid; and
   e. connecting the sample extraction device to an inlet on a microfluidic device.

21. The method of claim 20, wherein steps (b) and (d) are repeated one or more times.

22. The sample extraction device of claim 1, wherein the swab shaft is a breakable swab shaft comprising a scored breakpoint.

23. A method for sample extraction from a swab tip comprising the use of the sample extraction device of claim 22 comprising the steps of:
   a. opening the lid of the sample extraction device;
   b. inserting the swab tip through the squeezing structure and into the liquid medium;
   c. pulling the swab tip back out of the squeezing structure;
   d. breaking the breakable swab shaft at the scored breakpoint and allowing the swab tip to rest atop the squeezing structure;
   e. closing the lid of the sample extraction device by securing the lid to the sample extraction container; and
   f. connecting the sample extraction device to an inlet on a microfluidic device.

24. The method of claim 23, wherein steps (b) and (c) are repeated one or more times.

* * * * *